United States Patent
Carver et al.

(10) Patent No.: US 7,041,106 B1
(45) Date of Patent: May 9, 2006

(54) INTERPHALANGEAL FUSION PIN

(75) Inventors: Andrew Carver, Ross, CA (US);
Lowell S. Weil, Sr., Glenview, IL (US);
Tim Lessek, Warsaw, IN (US); William S. Pietrzak, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 233 days.

(21) Appl. No.: 09/882,320

(22) Filed: Jun. 15, 2001

(51) Int. Cl.
*A61B 17/56* (2006.01)

(52) U.S. Cl. .................. 606/72; 606/77; 623/21.11; 623/21.19

(58) Field of Classification Search ............ 606/77, 606/72, 65, 66, 67; 623/21.11, 21.12, 21.15, 623/21.16, 21.17, 21.19, 20.32, 20.27, 23.4, 623/23.39
See application file for complete search history.

(56) References Cited

U.S. PATENT DOCUMENTS

| | | | | | |
|---|---|---|---|---|---|
| 3,681,786 A | * | 8/1972 | Lynch | ................. | 128/DIG. 21 |
| 5,047,059 A | * | 9/1991 | Saffar | ....................... | 623/21.15 |
| 5,092,896 A | * | 3/1992 | Meuli et al. | ............. | 623/21.15 |
| 5,984,970 A | * | 11/1999 | Bramlet | ................... | 623/21.15 |
| 6,011,497 A | * | 1/2000 | Tsang et al. | .................. | 341/50 |
| 6,017,366 A | * | 1/2000 | Berman | ................... | 623/21.11 |
| 6,319,284 B1 | * | 11/2001 | Rushdy et al. | ............ | 623/18.11 |
| 6,386,877 B1 | * | 5/2002 | Sutter | .......................... | 433/173 |

* cited by examiner

*Primary Examiner*—Pedro Philogene
(74) *Attorney, Agent, or Firm*—Harness, Dickey & Pierce, P.L.C.

(57) ABSTRACT

A device is described for joining a first phalange to a second adjacent phalange, such as the proximal phalange to the intermediate phalange at the proximal interphalangeal joint. The device is a substantially elongated member comprised of a resorbable material, such as, but not limited to polylactic acid, polyglycolic acid, and combinations thereof. The member has a first end portion, a middle portion, and second end portion spaced and opposed from the first end portion. The middle portion has a curvature such that an angle is formed between the first end portion and the second end portion, wherein the angle is substantially anatomically correct with respect to the particular joint, such as the proximal interphalangeal joint.

27 Claims, 2 Drawing Sheets

INTERPHALANGEAL FUSION PIN

BACKGROUND

The present invention relates generally to bone pins, and more particularly, to a new and improved interphalangeal fusion pin which provides an anatomically correct angle between a first phalange and a second adjacent phalange, such as the proximal phalange and the intermediate phalange which exists at the proximal interphalangeal joint, wherein the pin is comprised of a resorbable material.

Digital deformities of the fingers and toes are some of the most common conditions encountered by orthopedists and podiatrists. Patients with digital deformities often experience significant pain from structural abnormalities. Some of these abnormalities are acquired, caused by traumatic injuries, neuromuscular pathologies, systemic diseases, or mechanical problems secondary to extrinsic pressures. The deformities are popularly known as either mallet finger, jersey finger, coach's finger, hammer toe, as well as a host of others indicative of several different pathologies.

Hammer toe is generally described in the medical literature as an acquired disorder, typically characterized by hyperextension of the metatarsophalangeal joint (MTPJ), hyperflexion of the proximal interphalangeal joint (PIPJ), and hyperextension of the distal interphalangeal joint (DIPJ). Although this condition can be conservatively managed (e.g., through the use of orthotic devices), in certain instances surgical intervention is required.

In order to prevent recurrence of the deformity and ensure the success of the surgical procedure, a proximal interphalangeal (PIP) joint arthrodesis is typically performed. The "end-to-end" or "peg-in-hole" techniques are the most commonly used procedures. The PIPJ is aligned with the rest of the toe in a corrected anatomical position and maintained in place by the use of a 0.045 Kirschner wire (K-wire) which is driven across the joint. Initially, the wire is placed from the PIPJ through the tip of the toe. It is then driven in retrograde fashion into the proximal phalanx. The exposed wire exiting the toe is bent to an angle greater than 90 degrees, and the bent portion is cut at 1 cm from the bend. At the conclusion of the surgical procedure, a small compressive dressing is placed around the toe, with a Jones compression splint being used for three to four weeks to protect the pin and the toe in order to maintain correction. The K-wire and the Jones splint are generally removed three weeks after surgery. Similar procedures may be followed to create arthrodesis of the distal interphalangeal joint (DIP) of the toe or for arthrodesis performed in the finger to correct digital abnormalities of the hand.

Although this type of surgical procedure has alleviated the discomfort of hammer toe and other abnormalities of the toe and finger joints for countless patients, the use of K-wire can result in the possible post-surgical misalignment of the phalanges (e.g., caused by distraction of the K-wire), as well as swelling, inflammation, and possible infection at the site of the exposed K-wire segment.

Of recent interest in the treatment of toe deformities, such as hammer toe, are prosthetic devices which have been used to treat deformities of the finger joints. For example, these devices can be inserted into adjoining phalanges of the finger and can serve to function ostensibly as a normal knuckle would. Because it is generally necessary to permit one or more of the joints of the finger to flex and bend, some of these devices are slightly angled to provide for an anatomically acceptable interphalangeal joint angle of the finger. Furthermore, some of these devices allow the joint portion to bend to a significant degree, thus permitting the finger a relatively wide range of articulation.

These devices are typically comprised of metallic or thermoplastic materials which, while being biocompatible, are also physiologically inert and thus are not resorbed by the body. There are, however, conditions in which an arthrodesis, or fusing of the affected finger or toe joint is desired, making a permanent device which is designed to permit joint flexion/extension inappropriate. Thus, the use of these permanent prosthetic devices in the treatment of hammer toe and other digital deformities, wherein the goal of the operation is arthrodesis, whereby the presence of the device would only be required for a short number of weeks to aid in maintaining correct anatomical alignment of the phalanges for fusion, would not be indicated. Additionally, these permanent devices would also be contraindicated in the treatment of certain finger conditions where the phalanges need to be correctly anatomically aligned for only a few weeks until a proper amount of healing for fusion has occurred.

Therefore, there exists a need for a new and improved bone pin which includes an anatomically correct angle between a first phalange and a second adjacent phalange, such as the proximal phalange and the intermediate phalange which exists at the proximal interphalangeal joint, wherein the pin is comprised of a resorbable material.

SUMMARY OF THE INVENTION

In accordance with a first embodiment of the present invention, a device for insertion into a first phalange and a second adjacent phalange so as to join the first phalange to the second phalange is provided, comprising a substantially elongated member comprised of a resorbable material. The member has a first end portion, a middle portion, and second end portion spaced and opposed from the first end portion. The middle portion has a curvature such that an angle is formed between the first end portion and the second end portion.

In accordance with a second embodiment of the present invention, a device for insertion into a first phalange and a second adjacent phalange so as to join the first phalange to the second phalange is provided, comprising a substantially elongated member comprised of a resorbable material. The member has a first end portion, a middle portion, and second end portion spaced and opposed from the first end portion. The first end portion and the second end portion have a surface portion for facilitating retention within the first phalange and the second phalange. The middle portion has a curvature such that an angle is formed between the first end portion and the second end portion. The angle is substantially anatomically correct.

In accordance with a third embodiment of the present invention, a method for joining a first phalange to a second adjacent phalange is provided, comprising providing a bore in a distal end of the first phalange, providing a bore in a proximal end of the second phalange, and providing a device comprising a substantially elongated member comprised of a resorbable material. The member has a first end portion, a middle portion, and second end portion spaced and opposed from the first end portion. The middle portion has a curvature such that the first end portion and the second end portion are angled towards one another. The device is inserted into the bore in the distal end of the first phalange and into the bore in the proximal end of the second phalange.

A more complete appreciation of the present invention and its scope can be obtained from the following detailed description of the invention, the drawings and the appended claims.

BRIEF DESCRIPTION OF THE DRAWINGS

The present invention will become more fully understood from the detailed description and the accompanying drawings, wherein.

The same reference numerals refer to the same parts throughout the various Figures.

DETAILED DESCRIPTION OF THE INVENTION

Although the present invention is directed primarily to the treatment of hammer toe conditions, it is equally applicable to any situation where a first phalange and a second adjacent phalange, of either a toe or a finger, are to be joined or fused together.

The use of various resorbable devices, such as pins, in connection with the treatment of various bone deformities, especially fractures, is fairly well known in the art. These resorbable devices, also referred to as bioresorbable, biodegradable, absorbable, and bioabsorbable devices, has enabled the medical community to achieve excellent surgical results, even under difficult clinical conditions.

The main benefit of using resorbable devices is that the devices are generally as strong as conventional metallic devices and resorb into the body over a generally predictable time period once a sufficient level of healing has occurred, for example, at the junction of a bone fracture, thus negating the need for subsequent removal of the device. By having the device resorb, the likelihood of osteolysis, stress fractures, and inflammatory immune system responses are greatly reduced.

One resorbable material of particular interest is marketed by Biomet, Inc. (Warsaw, Ind.) under the tradename LACTOSORB®. LACTOSORB® is a resorbable co-polymer synthesized from all-natural ingredients: 82% L-lactic acid and 18% glycolic acid. Unlike the homopolymers in common use such as 100% poly-L-lactic acid (PLLA) or 100% polyglycolic acid (PGA), LACTOSORB® copolymer is substantially amorphous (i.e., without crystallinity), meaning that its degradation is uniform, precluding the crystalline release associated with degrading copolymers that have been associated with late inflammatory reactions. Furthermore, the LACTOSORB® copolymer ratio permits the polymer to retain most of it's strength for six to eight weeks, which is appropriate for healing, but not so long as to raise concerns about long-term stress shielding of bone. Additionally, the mass of LACTOSORB® implants is completely eliminated by the body within about 9–15 months so as to eliminate concerns of long-term implant residence.

In accordance with one embodiment of the present invention, the device is preferably comprised of a resorbable material so that a subsequent procedure for removing the device is not needed, as is the case with permanent metallic or thermoplastic devices. In accordance with a preferred embodiment of the present invention, the resorbable material is comprised of polylactic acid, polyglycolic acid, and combinations thereof, but is not limited to this family of resorbable materials.

Figure 1:
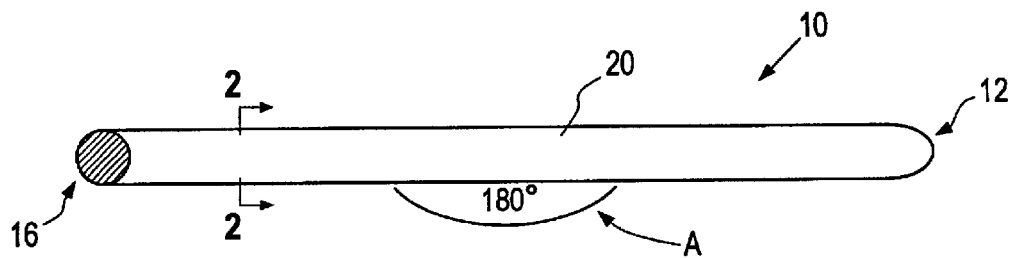
FIG. 1 illustrates a perspective view of a blank of resorbable material, in accordance with one embodiment of the present invention.
Figure 2:
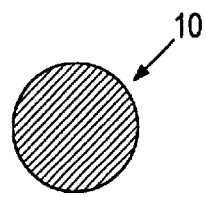
FIG. 2 illustrates a sectional view taken along line 2—2 of FIG. 1, in accordance with one embodiment of the present invention.
Figure 3:
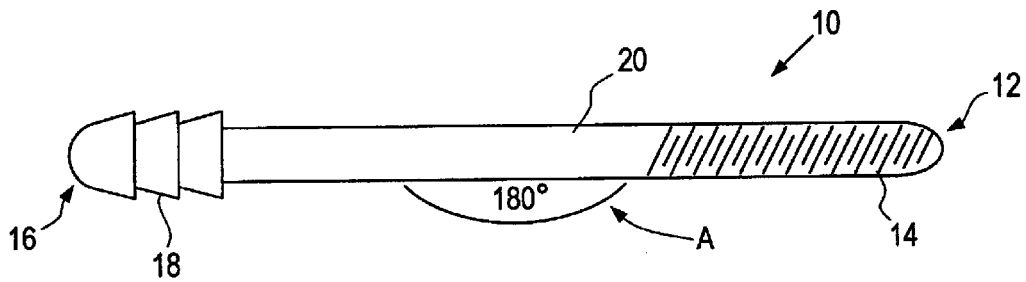
FIG. 3 illustrates a perspective view of the blank of FIG. 1 with threaded and shouldered surfaces formed thereon, in accordance with one embodiment of the present invention.
Figure 4:
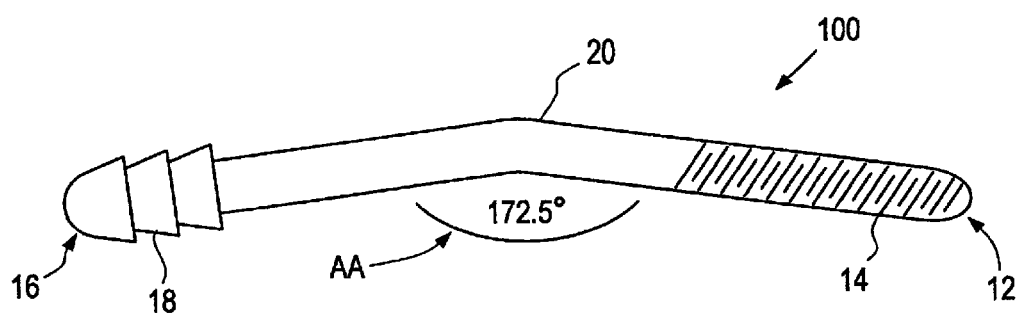
FIG. 4 illustrates a perspective view of the hammer toe pin device, in accordance with one embodiment of the present invention.

Referring to FIGS. 1–4, there is shown a blank 10 of a resorbable material that will eventually be formed into the device 100 of the present invention, shown specifically in FIG. 4. The blank 10 is preferably shaped in a substantially elongated and cylindrical configuration. Once the proper length of the blank 10 has been established, one end 12 of the blank 10 is preferably provided with a threaded surface 14 for facilitating insertion and retention into a proximal phalange. Preferably the other end 16 of the blank 10 is provided with a shouldered, ribbed or helical surface 18 for facilitating insertion and retention into a distal (or intermediate) phalange. Because the resorbable material can be shaped by heating and pressing, it is very easy to impart any number of types of surface structures thereon. Alternatively, the various surface structures can be machined upon the blank 10.

The blank 10 can now be shaped so as to impart an anatomically acceptable angle thereto. It will be appreciated that the pre-determined angle will depend, in part, on the particular phalanges that are to be joined or fused together. Additionally, it will also be appreciated that, due to the nature of the resorbable materials employed, it is possible to change the pre-determined angle if the situation arises.

As can be seen, the blank 10 initially has an angle A of 180 degrees between the two respective ends 12 and 16. However, the angle normally existing between the proximal phalange and the intermediate phalange in healthy individuals is less than 180 degrees, and probably about 172.5 degrees. The establishment of the anatomically acceptable angle AA can be accomplished by heating and then bending the blank 10 so as to cause a curvature to form preferably at or near the central portion 20 of the blank 10 so that the two respective ends 12 and 16 of the blank 10 are slightly drawn towards one another. Alternatively, the curvature can be produced by "cold working" the blank 10, that is, by imparting the curvature under ambient temperature conditions. In this manner, an anatomically acceptable angle M can be imparted to the device 100 so as to properly align the intermediate phalange with the proximal phalange after insertion of the device 100 at the PIPJ, or any other pair of adjacent phalanges.

It should be noted that it is not necessary to wait to impart the anatomically acceptable angle to the blank 10 until after the threaded and/or shouldered, ribbed or helical surfaces have been formed. For example, the blank 10 can first be bent to impart the correct anatomical angle, as previously described, and then the threaded and/or shouldered, ribbed or helical surfaces 14 and 18, respectively, could be formed on the two respective ends 12 and 16. Alternatively, the complete configuration of the device 100 can be produced in one step through injection molding.

Once the bending has occurred and the surface structures have been formed on the respective ends 12 and 16, the device 100 of the present invention, as shown in FIG. 4, is ready for insertion into the PIPJ. The device 100 has an angle AA of about 172.5 degrees formed between the two respective ends 12 and 16.

Figure 5:
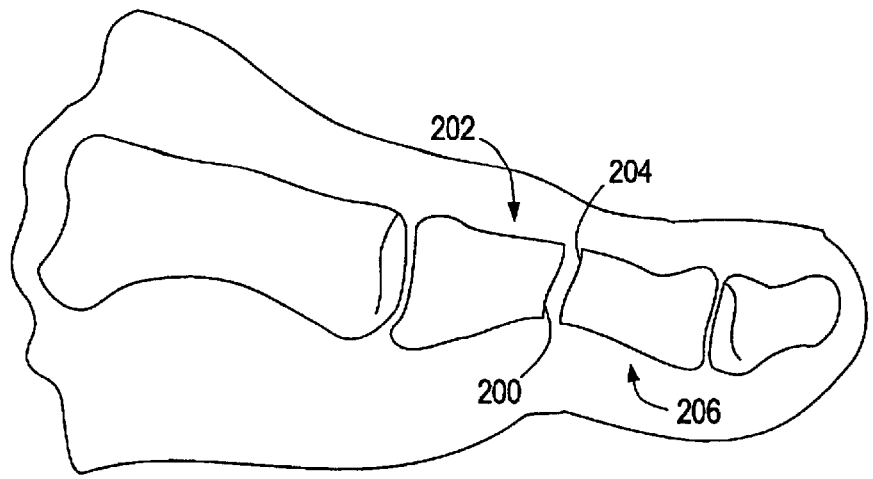
FIG. 5 illustrates a partial sectional view of a human foot about to undergo a PIPJ arthrodesis procedure, in accordance with one embodiment of the present invention.
Figure 6:
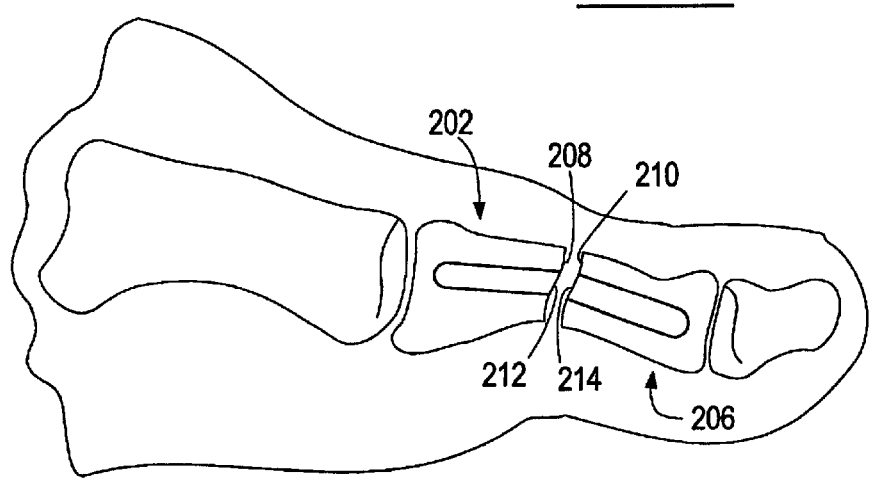
FIG. 6 illustrates a partial sectional view of a human foot that has undergone a PIPJ arthrodesis procedure with bores being drilled into the respective resected surfaces, in accordance with one embodiment of the present invention.
Figure 7:
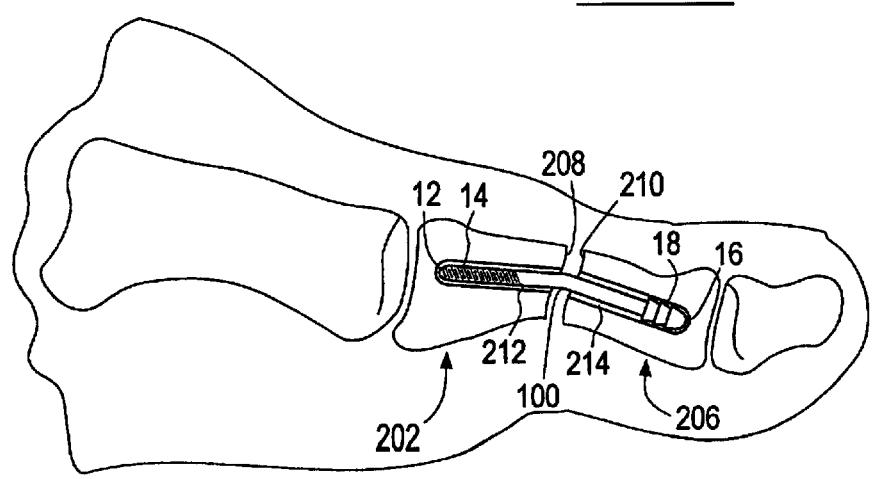
FIG. 7 illustrates a partial sectional view of a human foot that has had a hammer toe pin device in accordance with the general teachings of the present invention inserted into the bores of the respective resected surfaces, in accordance with one embodiment of the present invention.

A non-limiting example for inserting the device 100 into the PIPJ of a human foot will now be presented with reference to FIGS. 5–7. Those skilled in the art will appreciate that, in a PIPJ arthrodesis, the distal portion 200 of the proximal phalange 202 and the proximal portion 204 of the intermediate phalange 206 are typically resected. To prepare the respective surfaces 208 and 210 for insertion of the device 100, it is generally necessary to provide bores 212 and 214, respectively, in the respective phalanges 202 and 206 using a suitable device, such as a surgical drill. Once the bores 212 and 214 are provided, it is preferred that the threaded portion 14 of the device 100 is screwed into the bore 212 of the distal surface 208 of the proximal phalange 202 to a sufficient depth with the remaining portion of the device 100 being oriented in an anatomically correct position with respect to the intermediate phalange 206. The shouldered, ribbed or helical portion 18 of the device 100 is then inserted into the bore 214 of the proximal surface 210 of the intermediate phalange 206 to a sufficient depth. The respective bores 212 and 214 should not have a diameter so large as to prevent frictional or other types of physical engagement of the respective surfaces of the device 100, nor should the respective bores 212 and 214 have a diameter so small as to prevent insertion of the respective ends 12 and 16 of the device 100 thereinto. The device 100 will gradually resorb over a period of several weeks as the healing process progresses and concludes.

Because the device 100 is comprised of resorbable material, the surgeon is able to easily modify the predetermined or preformed angle or shape of the device 100, if the need is warranted. For example, perhaps the anatomically acceptable angle A of 172.5 degrees is unsuitable for a particular patient due to particular anatomical considerations. If the surgeon were using metallic hammer toe pins, for example, it would be very difficult, if not impossible, to alter the angle of curvature of the device. The surgeon would be forced to remove the hammer toe pin from the proximal phalange and then select another hammer toe pin having a different angle of curvature. With the interphalangeal fusion pin device of the present invention, the surgeon can easily adjust the angle of curvature to another degree (e.g., by heating and bending the device or even "cold working" the device) that is more suitable for that particular patient. Thus, the device 100 of the present invention is very versatile and adaptable to many different surgical scenarios and situations involving the treatment of finger and toe conditions, such as, but not limited to hammer toe.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention as defined by the claims that follow.

What is claimed is:

1. A method for inserting a device into a first phalange and a second adjacent phalange so as to fuse the first phalange to the second phalange, comprising:
   providing a monolithic substantially elongated member comprised of a resorbable material;
   connecting a first end portion to the first phalange, a middle portion, and connecting a second end portion with the second phalange spaced and opposed from the first end portion;
   adjusting a middle portion having a fixed angle to a second fixed angle such that the second fixed angle is formed between the first end portion and the second end portion.

2. The method according to claim 1, further comprising implanting the first end portion into a phalange selected from a group consisting of proximal phalanges, intermediate phalanges, distal phalanges.

3. The method according to claim 1, further comprising implanting the second end portion into a phalange selected from a group consisting of proximal phalanges, intermediate phalanges, distal phalanges, and combinations thereof.

4. The method according to claim 1, wherein the first end portion has a surface portion for facilitating insertion into a proximal phalange.

5. The method according to claim 4, wherein the surface portion comprises a threaded surface.

6. The method according to claim 1, wherein the first end portion has a surface portion for facilitating retention within a proximal phalange.

7. The method according to claim 6, wherein the surface portion comprises a threaded surface.

8. The method according to claim 1, wherein the second end portion has a surface portion for facilitating insertion into an intermediate phalange.

9. The method according to claim 8, wherein the surface portion comprises a structure selected from the group consisting of shoulders, ribs, helixes, and combinations thereof.

10. The method according to claim 1, wherein the second end portion has a surface portion for facilitating retention within an intermediate phalange.

11. The method according to claim 10, wherein the surface portion comprises a structure selected from the group consisting of shoulders, ribs, helixes, and combinations thereof.

12. The method according to claim 1, further comprising selecting the resorbable material is selected from the group consisting of polylactic acid, polyglycolic acid, and combinations thereof.

13. The method according to claim 1, wherein the member is substantially cylindrical.

14. The method according to claim 1, wherein the angle is substantially anatomically correct.

15. A method for an operative procedure for fusing a first phalange to a second adjacent phalange, comprising:
   providing a bore in a distal end of the first phalange;
   providing a bore in a proximal end of the second phalange;
   providing a device comprising a substantially elongated member comprised of a resorbable material;
   wherein the member has a first end portion, a middle portion, and second end portion spaced and opposed from the first end portion;
   wherein the middle portion has a bend formed during the operative procedure by a user such that the first end portion and the second end portion have a fixed angle towards one another; and inserting the device into the bore in the distal end of the first phalange and into the bore in the proximal end of the second phalange.

16. The method according to claim 15, wherein providing a bore includes providing a bore in the first phalange selected from a group consisting of proximal phalanges, intermediate phalanges, or distal phalanges.

17. The method according to claim 15, wherein providing a bore includes providing a bore in the second phalange selected from a group consisting of proximal phalanges, intermediate phalanges, or distal phalanges.

18. A method for inserting a device into a first phalange and a second adjacent phalange during an operative procedure so as to fuse the first phalange to the second phalange, comprising:
providing a substantially rigid elongated member comprised of a resorbable material;
engaging a first end portion of the member in the first phalange, a middle portion, and engaging a second end portion in the second phalange spaced and opposed from the first end portion;
forming a middle portion to have a fixed curvature and adjusting a fixed angle during the operative procedure between the first end portion and the second end portion.

19. The method of claim 15, wherein forming the curvature includes:
heating the middle portion to a selected temperature;
bending the middle portion; and
cooling the middle portion.

20. An apparatus to cause a fusion between two phalanges in a body, comprising:
a substantially single piece elongated cylindrical member having a first end and a second end interconnected by a middle portion;
a helical thread formed on the first end, wherein twisting the substantially single piece elongated cylindrical member is operable to advance the substantially single piece elongated cylindrical member into one of the two phalanges;
a barb extending from the second end of the substantially single piece elongated cylindrical member, wherein the barb engages the other of the two phalanges to assist in holding the substantially single piece elongated cylindrical member relative thereto.

21. The apparatus of claim 20, wherein the middle portion is operable to be deformed by a user during an implantation procedure.

22. The apparatus of claim 20, wherein middle portion is produced at a first angle and deformed by a user at a later time to a second angle prior to use of the apparatus.

23. The apparatus of claim 20, wherein the substantially single piece elongated cylindrical member is formed of a resorbable material.

24. A method for an operative procedure for fusing a first phalange to a second adjacent phalange with a resorbable device, comprising:
forming a bore in the first phalange;
forming a bore in the second phalange;
providing a thread on a first end of the device;
providing a barb on the second end of the device;
determining an appropriate angle between the first end to be positioned relative to the bore of the first phalange and the second end to be positioned relative to the bore of the second phalange during an operative procedure;
forming the determined angle in the device; threading the first end of the device into the bore of the first phalange; and
pushing the second end of the device including the barb into the bore formed in the second phalange.

25. The method of claim 24, wherein forming the angle includes forming an anatomically appropriate angle.

26. The method of claim 24, further comprising: forming the device as a substantially elongated cylinder.

27. The method of claim 24, further comprising:
forming the device material.

* * * * *